Figure 1:
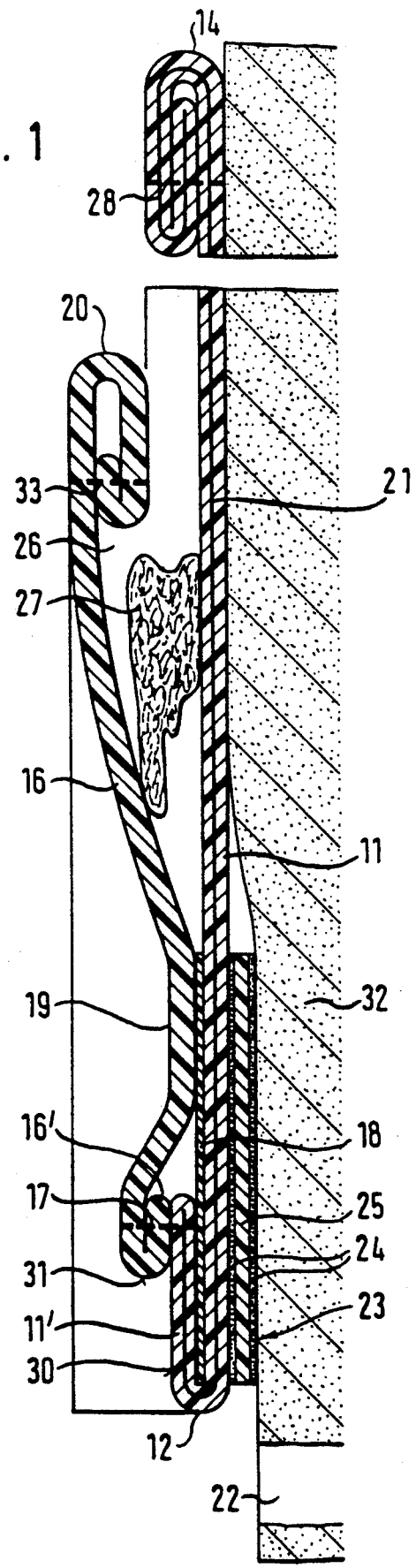

United States Patent [19]
Duncan et al.

[11] Patent Number: 5,203,350
[45] Date of Patent: Apr. 20, 1993

[54] MEDICAL SURGICAL COVER SHEET

[75] Inventors: John A. Duncan, Glenrothes; Suresh R. Patel, Dalgety Bay, both of Scotland; Günter Wiedner, Seeshaupt, Fed. Rep. of Germany

[73] Assignee: Rotecno AG, Zürich, Switzerland

[21] Appl. No.: 764,671

[22] Filed: Sep. 24, 1991

[51] Int. Cl.$^5$ .................. A61B 19/08; B32B 5/26
[52] U.S. Cl. ................................. 128/849; 128/852
[58] Field of Search ............... 128/849, 853, 854, 855

[56] References Cited

U.S. PATENT DOCUMENTS

| | | | |
|---|---|---|---|
| Re. 27,710 | 7/1973 | Melges | 128/853 X |
| 3,452,750 | 7/1969 | Blanford | 128/853 |
| 3,455,302 | 7/1969 | Liloia et al. | 128/849 |
| 3,538,912 | 11/1970 | Becker, III | |
| 3,721,234 | 3/1973 | Hadtke et al. | 128/853 X |
| 3,766,913 | 10/1973 | Balin | 128/853 |
| 3,871,693 | 3/1975 | Krzewinski | 128/853 |
| 3,955,569 | 5/1976 | Krzewinski et al. | |
| 4,027,665 | 6/1977 | Scrivens | |
| 4,089,331 | 5/1978 | Hartigan et al. | 128/853 X |
| 4,607,631 | 8/1986 | Hanssen | 128/853 |
| 4,616,642 | 10/1986 | Martin et al. | 128/853 |
| 4,711,236 | 12/1987 | Glassman | 128/854 |
| 4,715,366 | 12/1987 | Teeple | 128/849 |

FOREIGN PATENT DOCUMENTS

| | | |
|---|---|---|
| 0116124A1 | 11/1983 | European Pat. Off. . |
| 182766 | 5/1986 | European Pat. Off. ............ 128/849 |
| 0269207A2 | 6/1988 | European Pat. Off. . |
| 2405124A1 | 1/1975 | Fed. Rep. of Germany . |
| 8707403.6 | 9/1987 | Fed. Rep. of Germany . |
| 4021353A1 | 1/1992 | Fed. Rep. of Germany . |
| 2221395A | 2/1990 | United Kingdom . |
| 8102100 | 8/1981 | World Int. Prop. O. .......... 128/853 |

Primary Examiner—Danton D. DeMille
Assistant Examiner—Kevin Rooney
Attorney, Agent, or Firm—Townsend and Townsend Khourie and Crew

[57] ABSTRACT

A medical surgical cover sheet comprises a hydrophobic fabric (11) and a hydrophilic fabric or knitted structure (16) arranged thereon. A pocket can be formed between the hydrophilic and hydrophobic fabrics and can receive an absorbent material. Provision is made for stiffening the edge adjacent the surgical wound and for adhesively connecting the cover sheet to the patient's skin adjacent the site of the operation.

28 Claims, 3 Drawing Sheets

MEDICAL SURGICAL COVER SHEET

The invention relates to a medical surgical cover sheet comprising at least one textile construction consisting of endless synthetic threads which has, adjacent to the site of the operation, a surgical edge, which is preferably straight but may also be curved for special applications, and further edges which are likewise straight, the cover sheet being expediently rectangular.

In such medical surgical cover sheets it is important to have the best possible barrier to bacteria and freedom from fluffing. On the other hand, a cover sheet of this kind should be able to store and absorb liquid, at least in a certain region adjacent the site of the operation.

The object of the invention is thus to provide a medical surgical cover sheet of the initially named kind which is capable of being simply secured close to the site of the operation and is, on the one hand, well sealed relative to bacteria and fluff-free and, on the other hand, has a large liquid absorption capability at the outer side, i.e. at the side remote from the patient, without the simple handling being impaired.

In order to satisfy this object the present invention provides a medical surgical cover sheet of the initially named kind which is characterised in that the textile construction is hyrophobic and in that a hydrophilic fabric or knitted structure of endless synthetic threads is arranged on the hydrophobic fabric adjoining the surgical edge.

In this manner a liquid repellent fabric is located at the underside which is moreover so tightly woven that it is also well sealed against bacteria. At the outside there is in contrast a hydrophilic fabric or knitted structure which absorbs liquids coming from the outside during the operation and thus renders them innocuous for the environment. As both fabrics consist of endless synthetic fibers they are extremely free from fluff.

Both fabrics should in particular consist of plastics which are capable of being washed and sterilised.

The hydrophilic fabric or knitted structure should be so designed and formed, for example by a rib-like enlarged surface, that a liquid picked up by it does not escape sideways when subject to mechanical pressure loads and cannot be pressed through the hydrophobic fabric, which for this purpose should be correspondingly tightly woven and designed.

It is of particular advantage when the hydrophilic fabric or rigid structure first starts at a small distance from the surgical edge set forth in claim 2.

In general the two fabrics of the invention should be sewn together in the region of the edges. In order to avoid liquid or bacteria bridges through the hydrophobic fabric or between the hydrophilic and hydrophobic fabrics it is advantageous to provide an embodiment in which the hydrophobic fabric is turned over towards the outside at the surgical edge and the hydrophilic fabric is only sewn to the turned over strip. The seam is in particular formed in such a way that the hydrophilic fabric or knitted structure is turned over downwardly in the region of the seam and only the thereby formed turned over strip is sewn to the turned over strip of the hydrophobic fabric.

More particularly the hydrophobic fabric and its turned over edge are connected together by a weldable foil which is arranged therebetween and are preferably welded together or permanently areally connected in another manner. The weldable foil extends away from the surgical edge up to and beneath the hydrophilic fabric and the hydrophilic fabric is also connected to the hydrophobic fabric, and is in particular welded thereto, in the edge region which adjoins the surgical edge. In these embodiments the weldable foil or the fusible or adhesive material resulting therefrom has in particular a stiffening action for the edge.

It is of particular importance that as a result of the construction of the invention fraying of the cover sheet in the region of the surgical edge is effectively avoided.

In a particularly expedient design the hydrophilic fabric is not connected to the hydrophobic fabric, at least in a substantial region remote from the surgical edge and is in particular not connected thereto at the edge remote from the surgical edge. The connection between the hydrophobic and the hydrophilic fabrics only takes place in a comparatively narrow edge region directly adjoining the turned over strips of the hydrophobic fabric and also at the side edges. I.e. the two fabrics are not laminated together in the largest zone of their overlapping surfaces.

In this way one can for example form a pocket between the two fabrics which is closed towards the surgical edge but open at the opposite edge. This pocket has the advantage that it can then be filled with absorbent or absorbing material, in particular a hydrophilic material such as cotton or cellular material.

At the side edges the hydrophilic fabric is preferably sewn to the hydrophobic fabric, and indeed the fabrics are preferably turned over and sewn at the side edges and at the edge remote from the surgical edge.

The hydrophilic fabric preferably extends from the surgical edge only over a fraction of the length of the side edges, with this fraction particularly amounting to from 20 to 60% preferably 30 to 50% and in particular to about 40% of the length of the side edges.

The free edge of the hydrophilic fabric is preferably turned back on itself and sewn to ensure that it is also free of fluffing here.

One of the two fabrics, preferably the hydrophobic fabric, is preferably made permanently antistatic, for example through inwoven conductive threads. In this way the cover sheet can be made permanently antistatic.

A strip adjoining the surgical edge and preferably of 0.5 to 5 cm, in particular 1 to 4 cm and expediently 3 cm width is advantageously welded, in particular through the weldable foil, so that it is still flexible but longer creasable. This results in a stiffening of the cover sheet in the region of this strip. In addition an adhesive tape in the form of a carrier foil with adhesive layers on both sides can be arranged without problem in the region of the surgical edge by means of which the cover sheet can be stuck to the patient's skin at the surgical edge.

The cover sheet of the invention thus has a comparatively stiff and defined edge in the region of the surgical edge which makes it possible to sealingly secure the sheet to the skin of the patient in this region.

The edges of the cover sheet which lie outside of the actual site of the operation are generally turned over and sewn together.

Figure 2:
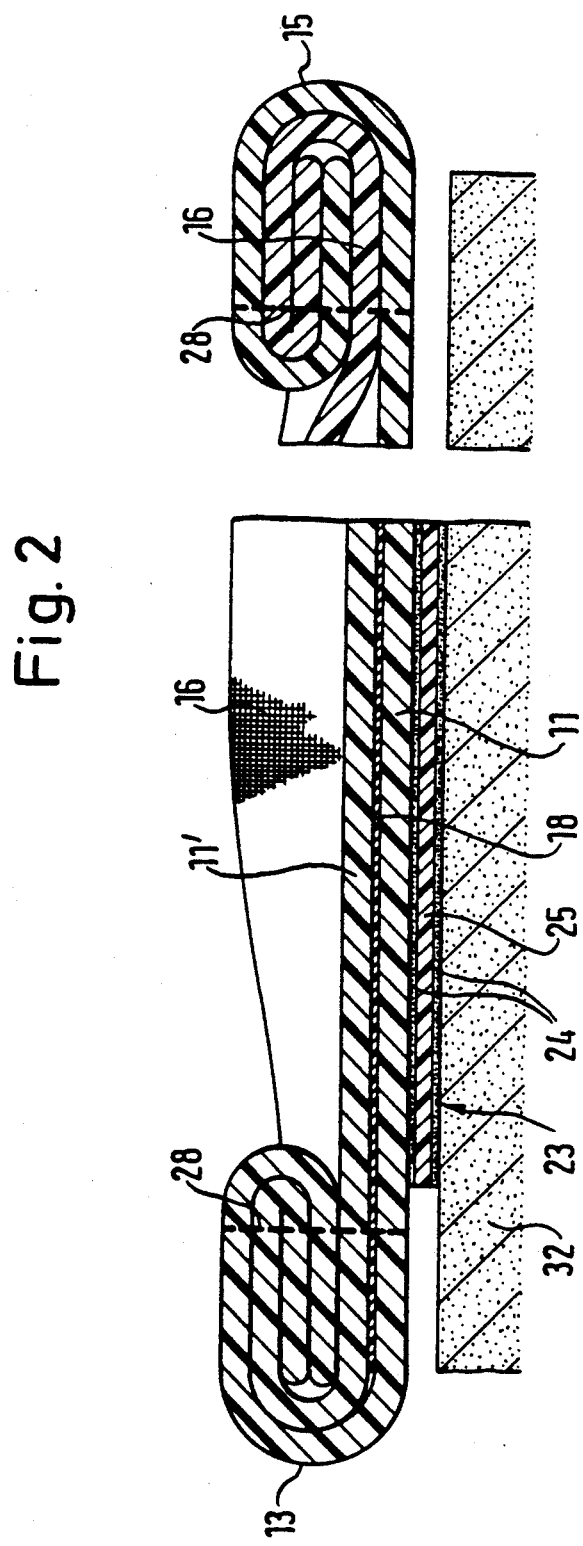
Figure 3:
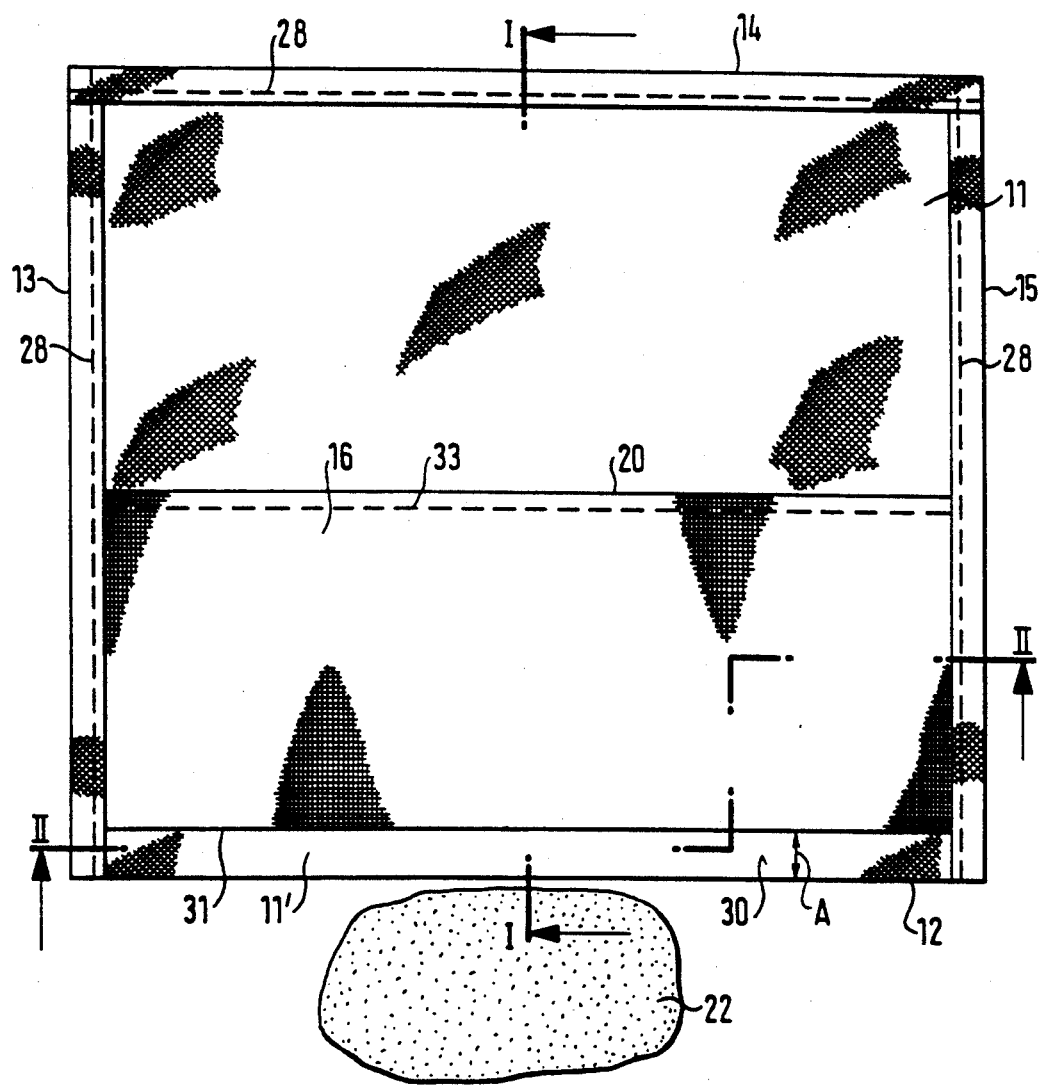

The invention will now be described in the following with reference to the drawings in which are shown:

FIG. 1 a section through a surgical cover sheet in accordance with the invention and in accordance with the line I—I of FIG. 3, FIG. 2 a section perpendicular to FIG. 1 of a surgical cover sheet in accordance with the invention and in accordance with the line II—II in FIG. 3, and FIG. 3 a plan view on a surgical cover sheet in accordance with the invention as seen from the outside.

In accordance with FIG. 3 the surgical cover sheet of the invention has a rectangular bacteria tight hydrophobic fabric Il of endless synthetic threads. A likewise rectangular hydrophilic fabric 16 is arranged over the lower half of the hydrophobic fabric 11 as seen in FIG. 3 and is likewise woven or knitted of endless synthetic threads.

The side edges 13, 15 and also the top edge 14 of the fabrics 11, 16 are turned over and sewn by normal seams 28, so that fluff-free edges are present. In similar manner the upper edge 20 of the hydrophylic fabric 16 is turned over and is likewise sewn by a normal seam 33.

The type of the turnover and the sewing is evident from FIG. 2.

As seen in FIGS. 1 and 3 the hydrophobic fabric 11 is turned back on itself in the region of the surgical edge 12 adjacent the site of the operation 22, so that a turned over strip, i.e. a hem 11' is formed. A weldable foil 18 is laid between the fabric 11 and the turned over strip 11' (FIGS. 1 and 2) which extends away from the surgical edge 12 beyond the turned over strip 11' up to a comparatively narrow edge region 19 of the hydrophilic fabric 16.

The turned over strip 11' is sewn, in a manner which can be seen from FIG. 1 with a downwardly turned turn over edge 16' of the hydrophilic fabric 16 by a seam 17 which thus extends neither through the fabric 11 nor through the fabric 16 but rather only through the turned over strips 11', 16'. For this region a liquid bridge through the sheet is avoided in this region.

It is important, that a narrow strip 13 of approximately 0.5 to 3 cm remains between the surgical edge 12 and the edge 31 of the hydrophilic fabric 16 adjacent the surgical edge 12 which, although it is located on the side remote from the patient 32 is hydrophobic. The hydrophilic region only starts following this where the hydrophilic fabric 16 is provided.

The turned over strip 11' and the edge strip 19 of the hydrophilic fabric 16 are so welded by means of the weldable foil 18 with the part of the hydrophobic fabric 11 which lies thereunder that on the whole a stiffened edge 12 is formed which has a width corresponding to the width of the turned over strip 11 and of the adjoining edge region 19.

In this region a double adhesive strip 23 comprising a carrier foil 25 with adhesive layers 24 on both sides can be attached without problem from below by means of which the edge region which adjoins the surgical edge 12 can be adhered to the skin of the patient 32, as can be seen from FIGS. 1 and 2.

At the side of the edge region 19 remote from the surgical edge 12 the hydrophilic fabric 16 is not connected with the hydrophobic fabric 11 by the seams 28, other than in the region of the side edges 13, 15 (FIG. 3) so that, in accordance with FIG. 1, a pocket 26 is formed which is bounded on the side remote from the surgical edge 12 by the edge 20 of the hydrophilic fabric 16. In the region of the edge 20 the hydrophilic fabric 16 is turned over twice and is sewn with a seam 33 so that freedom from fluffing is ensured in this region. Conductive threads 21 are woven into the hydrophobic fabric 11 in accordance with FIG. 1 in order to made the fabric permanently antistatic.

An absorbent material such as cotton or cellular material can be introduced into the pocket 26 in accordance with FIG. 1.

The use of the surgical cover sheet in accordance with the invention proceeds as follows:

Before the start up or also during the operation the surgeon decides whether the pocket 26 should or should not be filled with liquid absorbent material 27. If required the absorbent material 27 is first introduced into the pocket 26.

As a rule, an adhesive strip 23 in accordance with FIGS. 1 and 2 is already secured to the lower side of the hydrophobic fabric 11 in the region of the turned over strip 11' and of the edge region 19 during packing, i.e. even prior to sterilisation of the surgical set. By means of this adhesive strip the relevant edge region of the cover sheet is then adhered to the skin of the patient 12 close to the site of the operation 22. As the edge region 11', 19 can be made comparatively stiff through the weldable foil 18 the cover sheet can be secured to the patient at the desired position without problem.

From now on no germs or bacteria can any longer penetrate from the patient's skin through the hydrophobic fabric, whereby the critical site 22 of the operation is largely protected from bacteria and germs.

On the other hand, when liquid is present during the operation, such as blood, wound water, wound secretion or flushing liquid which gets onto the upper side of the cover sheet of the invention it can be absorbed by the hydrophilic fabric 16 and also by the absorbent material 27. In this way reinfection due to liquids which are sprayed around or flow back can be avoided.

The hydrophobic fabric 11 is preferably a fine filamentary (microfilament) polyester fabric with a hydrophobic finish, for example "Rophobo" (registered trademark of the Applicants).

The hydrophilic fabric 16 can be formed accordingly but with a hydrophilic finish, for example "Rophilo" (registered trademark of the Applicants). A fabric or woven structure can also be used which has an enlarged effective surface through a type of rib structure and which is suitable for lateral movement of the picked up liquid on the exertion of mechanical pressure. Furthermore, fabrics or woven structures of hollow fibers can be used with particular advantage as a hydrophilic fabric.

Four cover sheets in accordance with the invention are mounted in overlapping manner in a generally rectangular arrangement around the site of the operation which is located at the middle. In many cases it is however sufficient to use a smaller number of cover sheets which can in particular be matched shapewise to the special conditions of a particular operation.

We claim:

1. A medical surgical cover sheet for covering at least part of a patient during an operation comprising:
   a hydrophobic textile construction comprised of fibers made of a synthetic material and having a plurality of edges, said edges including a surgical edge for placement proximate to a site on a patient where the operation is to take place and a side edge;
   a hydrophilic textile fabric comprised of fibers made of a synthetic material arranged on the hydrophobic construction in a vicinity of the surgical edge; and
   a surgical strip formed by a turned-over section of the hydrophobic construction at the surgical edge, said section being turned over towards an outside surface of the hydrophobic construction;

the hydrophilic fabric being sewn to the turned over strip forming a seam.

2. The cover sheet of claim 1 wherein the surgical edge is straight.

3. The cover sheet of claim 1 wherein the hydrophilic fabric is a knitted fabric.

4. The cover sheet of claim 1 wherein at least one of the edges is curved.

5. The cover sheet of claim 1 wherein the cover is rectangular in shape.

6. The cover sheet of claim 1 wherein the hydrophilic fabric has an edge closest to the surgical edge which is spaced a distance 0.5 to 3 cm from the surgical edge.

7. The cover sheet of claim 6 wherein the distance is approximately 2 cm from the surgical edge.

8. The cover sheet of claim 1 further comprising:
an inner strip formed by a turned-over section of the hydrophilic fabric, said section being turned-over towards an inside surface of the hydrophilic fabric;
the inner strip of the hydrophilic fabric being sewn to the surgical strip.

9. The cover sheet of claim 1 further comprising a weldable foil arranged between the hydrophobic construction and the surgical strip.

10. The cover sheet of claim 9 wherein the hydrophobic construction and the surgical strip are connected together by means including welding.

11. The cover sheet of claim 9 further comprising:
a means for connecting the hydrophobic construction and the hydrophilic fabric; and
the weldable foil is dimensioned so as to extend from the surgical edge of the hydrophobic construction to an underside of the hydrophilic fabric.

12. The cover sheet of claim 11 wherein the hydrophobic construction is welded to the hydrophilic fabric in an edge region in a vicinity of and spaced from the surgical edge.

13. The cover sheet of claim 1 further comprising:
a surgical strip formed by a turned-over section of the hydrophobic construction, said section being turned over towards an outside surface of the construction at the surgical edge;
the hydrophobic construction being unsecured to the hydrophilic fabric in a region of the surgical edge, wherein the hydrophobic construction and the hydrophilic fabric are secured to each other at a narrow edge region adjoining the surgical strip of the hydrophobic construction and at the side edge.

14. The cover sheet of claim 1 wherein the hydrophilic fabric is sewn to the hydrophobic construction proximate to the side edge.

15. The cover sheet of claim 1 further comprising:
a hydrophobic side strip formed by turning over a side edge of the hydrophobic construction and means securing said strip to the construction;
a hydrophilic side strip formed by turning over a side strip of the hydrophilic fabric and means securing said strip to the fabric; and
the hydrophobic construction and the hydrophilic fabric being secured to each other by means securing the hydrophobic side strip to the hydrophilic side strip.

16. The cover sheet of claim 15 wherein the securing means comprises sewing.

17. The cover sheet of claim 1 wherein the hydrophilic fabric is dimensioned to extend from the surgical edge over about 20% to 60% of the length of side edges of the construction.

18. The cover sheet of claim 1 wherein the fabric extends over about 40% of the length of said side edges.

19. The cover sheet of claim 1 wherein the hydrophilic fabric has a turned-over strip sewn at an edge remote from the surgical edge.

20. The cover sheet of claim 1 including means connected with at least one of the hydrophobic construction and the hydrophilic fabric for rendering said at least one of the construction and fabric permanently antistatic.

21. The cover sheet of claim 20 wherein the antistatic means comprises in-woven conductive threads.

22. The cover sheet of claim 1 further comprising a flexible crease-resistant strip comprised of a turned-over strip of the hydrophobic construction adjoining the surgical edge, and a length of weldable foil positioned on a surface of the crease-resistant strip, the foil and the strip secured together by welding.

23. The cover sheet of claim 22 wherein the strip welded to the foil is approximately 3 cm in width.

24. The cover sheet of claim 1 further comprising:
an adhesive strip including an adhesive layer on a side of a carrier foil,
said adhesive strip attached close to and substantially parallel to the surgical edge on an underside of the hydrophobic construction and said layer facing away from the construction.

25. The cover sheet of claim 1 further comprising:
a pocket formed from the hydrophobic construction and the hydrophilic fabric such that said pocket is closed towards the surgical edge and open at an opposite edge.

26. The cover sheet of claim 25 including an absorbent material arranged in the pocket.

27. The cover sheet of claim 26 wherein the material is cellular.

28. The cover sheet of claim 27 wherein the cellular material is cotton.

* * * * *